(12) United States Patent
Kuan et al.

(10) Patent No.: US 8,692,193 B2
(45) Date of Patent: *Apr. 8, 2014

(54) METHOD FOR INSPECTING EUV RETICLE AND APPARATUS THEREOF

(75) Inventors: Chiyan Kuan, Danville, CA (US); Wei Fang, Milpitas, CA (US); You-Jin Wang, Milpitas, CA (US)

(73) Assignee: Hermes Microvision, Inc., Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,702

(22) Filed: May 24, 2012

(65) Prior Publication Data

US 2012/0228494 A1  Sep. 13, 2012

Related U.S. Application Data

(63) Continuation-in-part of application No. 12/850,899, filed on Aug. 5, 2010, now Pat. No. 8,217,349.

(51) Int. Cl.
*G01N 23/225* (2006.01)
*H01J 37/28* (2006.01)

(52) U.S. Cl.
CPC ............ *G01N 23/2251* (2013.01); *H01J 37/28* (2013.01); *H01J 2237/2817* (2013.01)
USPC .......................................... 250/307; 250/310

(58) Field of Classification Search
USPC ................................................ 250/307, 310
See application file for complete search history.

(56) References Cited

U.S. PATENT DOCUMENTS

| 6,002,740 | A  | * | 12/1999 | Cerrina et al. ................... 378/43 |
|-----------|----|---|---------|-------------------------------------------|
| 7,759,653 | B2 | * | 7/2010  | Chen et al. ............. 250/396 ML       |
| 8,217,349 | B2 | * | 7/2012  | Kuan et al. ..................... 250/310  |
| 8,592,102 | B2 | * | 11/2013 | Lin et al. ........................... 430/5|
| 2002/0035461 | A1 | * | 3/2002 | Chang et al. ..................... 703/13  |
| 2008/0302963 | A1 | * | 12/2008 | Nakasuji et al. .............. 250/310     |
| 2008/0302964 | A1 | * | 12/2008 | Shinada et al. ............... 250/310     |
| 2009/0101816 | A1 | * | 4/2009  | Noji et al. ..................... 250/310  |
| 2009/0206252 | A1 | * | 8/2009  | Okazaki et al. ............... 250/307     |
| 2010/0019147 | A1 | * | 1/2010  | Hatakeyama et al. ........ 250/307         |
| 2013/0126728 | A1 | * | 5/2013  | Waiblinger et al. ........... 250/305      |

OTHER PUBLICATIONS

Sterling Watson, Dave Alles, Gregg Inderhees; Electron Beam Inspection of NGL Reticles; KLA Tencor, EUVL Symposium Kobe, Oct. 18, 2010, pp. 1-20.

* cited by examiner

*Primary Examiner* — Jack Berman
*Assistant Examiner* — Eliza Osenbaugh-Stewart
(74) *Attorney, Agent, or Firm* — Rosenberg, Klein & Lee (57) ABSTRACT

A method of inspecting an EUV reticle is proposed, which uses an original design layout information to align the plurality of patterns on an image, which is got by scanning the surface of an EUV reticle, such that the defect can be identified and classified according to the aligned patterns. In the scanning process, a step of conditioning surface charge is followed by a step of inspecting surface of the EUV reticle wherein the step of conditioning surface can neutralize the surface charge and the step of inspecting can obtain an image of the EUV reticle. The method of inspecting an EUV reticle also tuning a retarding electrode to attract more secondary electrons such that the greylevels of different patterns may be shown and the defect can be identified and classified.

32 Claims, 7 Drawing Sheets

METHOD FOR INSPECTING EUV RETICLE AND APPARATUS THEREOF

This is a continuation-in-part of application Ser. No. 12/850,899, filed Aug. 5, 2010, currently pending.

BACKGROUND OF THE INVENTION

Lithography process is usually used in a semiconductor process, which transfers the patterns of masks to a wafer in layer by layer and then a chip is formed later. If the mask has a defect, the defect is also transferred to the wafer, so the mask inspection, before manufacturing semiconductor, is applied to avoid transferring the defect of the mask. Lots of mask inspection techniques have been developed.

The lithography technique keeps developing and getting smaller, and now the nano-level technology has been developed, such as the extreme ultraviolet (EUV), but the technology is not ready, because the nano-level mask inspection technique and tool are not prepared and valid. In nano-level scale inspection of the mask, EUV reticle, the conventional optical inspection technology can not satisfy the requirement of the high resolution generally. To increase the energy of X-ray (high frequency X-ray) can improve the resolution. However, high energy X-ray inspection may damage the EUV reticle. Some proposed approaches of nano-level mask inspection technique are discussed as follows:

In US20080318138, one side of the mask is coated by a reflection layer and the other side is coated by a conductive layer. To detect the transmitted light and the reflected light and then constitute an image of the EUV reticle to enhance the contrast of a detected image of the EUV reticle. That can enhance the accuracy of inspecting the EUV reticle, but make the process of manufacturing an EUV reticle more complex.

In U.S. Pat. Nos. 7,440,093 and 7,271,891, a susceptibility material is formed on the reticle and then the defects (if existed) will has different susceptibility. The susceptibility of different areas of the EUV reticle should be different and then a susceptibility map of the EUV reticle could be reconstruct by the different susceptibility of different areas, so the defects of the EUV reticle can be inspected. That inspects the EUV reticle indirectly but directly and the susceptibility material of the EUV reticle also makes the process of manufacturing an EUV reticle more complex.

In US20070064997, two separate inspection steps are used. An optical inspection is firstly used to inspect the EUV reticle for finding out the defect areas in a larger scale, and the optical inspection has a rough resolution. Then an electron beam (EB) inspection is used to inspect the defect areas to find out the precise defect with high resolution of inspecting the defect of the EUV reticle. Two inspection tools are used in the prior art to have a complex inspection process, and the energy of the EB inspection may be too large to damage the EUV reticle. For example. The energy of an EB used in inspecting the EUV reticle is high to 50KV, and so high energy will damages the EUV reticle. Besides, the surface charge of the EUV reticle is not processed in this prior art, which may distort the result of the inspection to reduce the accuracy thereof.

In U.S. Pat. No. 7,090,948, a buffer layer is disposed on a hard mask. The buffer layer is transferred into a hard mask in an etching process. In an initial inspection, defects are found and the then the hard mask can be transferred into the reflection layer for repairing the EUV reticle. The invention provides a mechanism of repairing a mask but not the mechanism of inspecting the EUV reticle. Although accompanying with the atomic force microscope, the skill is used to check the alignment of the EUV reticle, which does not inspect the EUV reticle.

In U.S. Pat. No. 7,407,729, a buffer layer with hard magnetic material is coated on a Bragg reflector on substrate of an EUV reticle and an absorber layer with soft magnetic material is coated on the buffer layer. Finally an imaging process is made with respect to the magnetic properties of the EUV reticle. Accordingly that makes the process of manufacturing the EUV reticle more complex, and the cost thereof is increased.

In U.S. Pat. No. 6,620,563, an atomic force microscope (AFM) is used to check the alignment of the EUV reticle, which also does not inspect the EUV reticle.

In U.S. Pat. No. 7,179,568, a dye material is incorporated in a photoresist layer and then exposed under radiation source, such as EUV or X-ray (Cu k-α(.alpha.)). The incident beam and the reflected beam will be combined to form an exposure curve in an intensity-position system. The exposure is insufficient at the positions of the defects in a critical exposure period, and the exposure curve in the intensity-position system will be reduced and less than a critical threshold value. The exposure below the critical threshold will be related to the defects of the EUV reticle, and the corresponding positions are located. Similar with the mentioned-above prior arts, a dye material and a photo-resist layer are introduced and that increases the complexity of manufacturing the EUV reticle.

In U.S. Pat. No. 6,555,828, an about 13 nm EUV is projected and three possible phenomena will can occur, an intensity reduction, an off-specular direction and a change of amplitude and phase of the electric field at the surface. These effects will reduce the reflected photoemission beam, which causes a reduction of a related EUV light, and the defect of the EUV reticle can be determined by observing the reduction of EUV light.

In US20020035461, an algorithm is used to find out defects according to an inspection of an EUV reticle. The algorithm calculates and defines an image and then compares the ideal image to find out the defects. That uses an algorithm to find the defect but not to directly inspect the defects of the EUV reticle.

Other prior arts inspect the defects of an EUV reticle by using EUV LASER pulse, and these arts have thermal and resolution issues usually.

According to the above discussion, a direct, efficient, simple and accuracy inspection of an EUV reticle is an important topic. The present invention proposes a method and an apparatus for inspecting the defects of the EUV reticle, the method and apparatus have these advantages, and the detailed is as follows.

SUMMARY OF THE INVENTION

The present invention is directed to a method for inspecting an EUV reticle that the defects come from the cap layer or the reflective layer of the EUV reticle may be easy to identify.

The present invention is directed to a method for inspecting an EUV reticle that can inspect a nano-scale EUV reticle. Electron beam (EB) is controlled under low current density and high speed, and the EB can be implemented to scan the surface of EUV reticle for inspecting EUV reticle.

The present invention is also directed to a method for inspecting an EUV reticle by using a scanning electron microscope (SEM). The SEM can provide electron beams and control the electron beams for inspecting the surface of an EUV reticle and for conditioning the surface charge of the EUV reticle.

The present invention is also directed to a method for inspecting an EUV reticle without accumulation of the surface charge of the EUV reticle. In inspecting the EUV surface, the number of primary electron is equal to the number of secondary electron by controlling the landing energy.

The present invention is also directed to an apparatus capable of inspecting an EUV reticle. The apparatus can be implemented by a SEM, a swing objective retarding immersion lens (SORIL) SEM or an improved SORIL SEM.

The present invention is also directed to a method for inspecting an EUV reticle without occurring the reflectivity loss of the EUV reticle.

In one embodiment, the method for inspecting an EUV reticle uses a scanning electron microscope (SEM) to scan an EUV reticle to get an image with a plurality of patterns thereon, and original design layout information is used to align the plurality of patterns, so as to determine and identify the defects according to the plurality of aligned patterns.

In another embodiment, the method for inspecting an EUV reticle comprises: using a primary beam emitting primary electrons to condition surface charge of a surface of the EUV reticle; using a focused primary beam to scan the surface of the EUV reticle which emit secondary electrons; detecting the secondary electrons from the surface of the EUV reticle to get an image with a plurality of patterns thereon; receiving an original design layout information to align the plurality of patterns; and determining and identifying the defects according to the plurality of aligned patterns.

In another embodiment, the method for inspecting an EUV reticle comprises: scanning an EUV reticle by using a scanning electron microscope (SEM) to get an image with a plurality of patterns thereon, wherein a retarding electrode in the SEM is tuned to attract more secondary electrons emitted from the EUV reticle; and determining and identifying the defects according to the plurality of the patterns.

In one embodiment, the method of inspecting an EUV reticle uses a primary beam for conditioning surface charge of the EUV reticle and a focused primary beam for inspecting the EUV reticle. In inspecting, a focused primary beam is injected into the surface of the EUV reticle and induces a secondary beam from the surface of the EUV reticle. The landing energy of the focused primary beam can be adjusted such that the number of secondary electron equals to the number of the primary electron of the primary beam to avoid accumulation of the surface charge. Then, a detector collects the electrons of the secondary beam to get the information of the surface of the EUV reticle. Finally, the information of the surface of the EUV reticle is compared with original design layout information, such as graphic data system (GDS) or open artwork system interchange standard (OASIS), to determine and identify the defects on the surface of the EUV reticle.

In another embodiment, the method of inspecting an EUV reticle uses a SEM to condition surface charge of a surface of the EUV reticle. The condense lens module of the SEM can be tuned by adjusting the electrostatic field/magnetic field or adjusted the position of the sample stage, or provided by a flood gun. Continuously, the formed primary beam can be used to scan the EUV reticle for conditioning the surface charge of the EUV reticle.

In another embodiment, the method of inspecting an EUV reticle comprises: conditioning surface charge of a surface of an EUV reticle by using a primary beam; injecting a focused primary beam to the surface of the EUV reticle, wherein the focused primary beam is adjusted to produce a low surface current density on the surface of the EUV reticle so that a reflectivity loss of the EUV reticle is controlled due to the low surface current density; and receiving a secondary electron beam from the surface of the EUV reticle.

In another embodiment, the method of inspecting an EUV reticle comprises: conditioning surface charge of a surface of an EUV reticle by using a primary beam; injecting a focused primary beam to the surface of the EUV reticle, wherein the focused primary beam is adjusted to produce a low surface current density on the surface of the EUV reticle, and the low surface current density on the surface of the EUV reticle is less than a value of 2.5325 $nA/nm^2$; and receiving a secondary electron beam from the surface of the EUV reticle.

In another embodiment, the apparatus for inspecting an EUV reticle may be implemented by a SEM, a swing objective retarding immersion lens SEM (SORIL SEM) or an improved SORIL SEM.

DESCRIPTION OF THE EXEMPLARY EMBODIMENTS

Embodiments of the method of inspecting the EUV mask or reticle and the apparatus thereof are described herein with reference to the attached drawings. The drawings are merely illustrative, and in no way limit the claims to what is illustrated.

Figure 1:
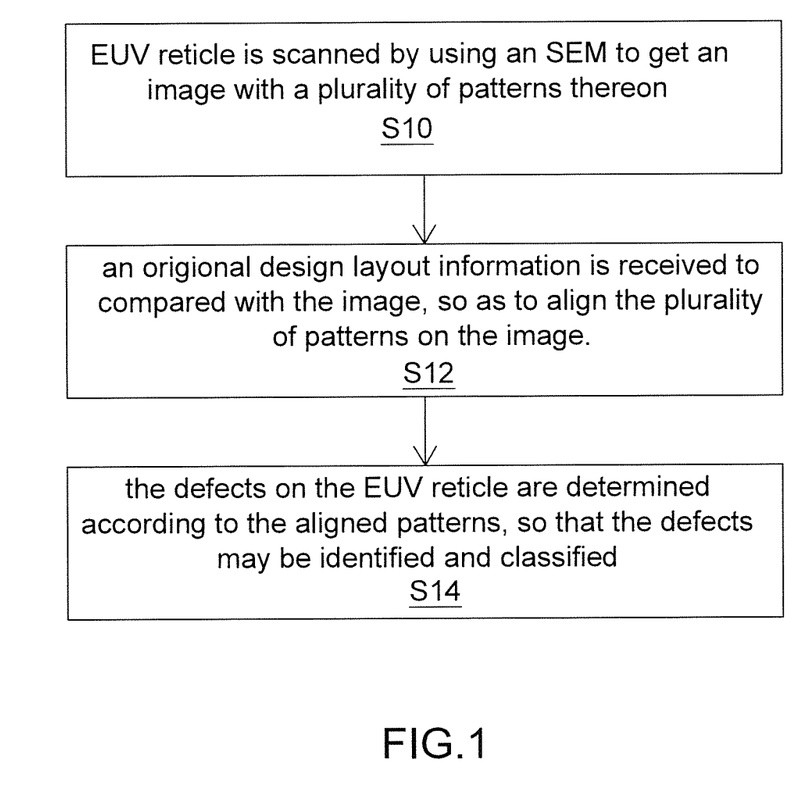
FIG. 1 is a flow chart for illustrating the method for inspecting an EUV reticle according to an embodiment of the present invention.

FIG. 1 is a flow chart for illustrating the method for inspecting an EUV reticle according to an embodiment of the present invention.

In step of S10, the EUV reticle is scanned by using a scanning electron microscope (SEM) to get an image with a plurality of patterns thereon. Here, the plurality of patterns may be holes, circuits, devices, or any combination thereof. In one embodiment, a cap layer and a reflective layer, made of the same or different metal, are formed on a substrate of the EUV reticle, and portion of the plurality of patterns may distribute on the cap layer and the reflective layer.

In step of S12, an original design layout information, such as graphic data system (GDS) or open artwork system interchange standard (OASIS), is received to compare with the image got from the SEM, so as to align the plurality of patterns on the image.

In step of S14, the defects on the EUV reticle are determined according to the plurality of aligned patterns, so that the defects may be identified and classified. In one embodiment, the defects, which come from the cap layer or the reflective layer, may be easy to identify.

According to an aspect of the present invention, in the scanning step of S10, electron beam(s) (EB) is/are used to scan and inspect the EUV reticle under the following condition, high energy and low electron density of the EB. The high energy electron can reach high resolution when inspecting the EUV reticle, such as nano-level inspection. The low electron density of the EB can avoid damaging the EUV reticle in inspection. In one embodiment, an electron beam source may be excited by a low current intensity and a high voltage to provide the low density and high speed electron beam. In one embodiment, a heated cathode is used, the heated cathode emits electrons and the electrons are accelerated by an imposed voltage. To decrease the current passing the heated cathode and increase the imposed voltage can provide the low density and high speed electron flow. The electron flow flies forward and passes the aperture of an aperture module to form the electron beam.

According to an aspect of the present invention, in the scanning step of S10, a primary electron beam is used to condition the surface charge of the EUV reticle and a focused primary electron beam is used to inspect the EUV reticle. In inspecting the surface of the EUV reticle, some charges may be accumulated on the surface of the EUV reticle, or the focused primary electron may cause a non-uniform charge distribution. The accumulation of the surface charge and the non-uniform charge distribution may distort or affect the focused primary electron beam in inspecting the EUV reticle, and reduce the inspection accuracy. A process of conditioning surface-charge is used to neutralize the surface charge or regulate the surface charge to a uniform charge distribution (a uniform surface voltage), called a Pre-Conditioning process. An electron primary charged particle beam can be used to scan the surface of an EUV reticle for conditioning the surface charge.

In the scanning step of S10, a step of inspecting surface EUV reticle continuously follows the step of conditioning surface charge. A focused primary beam is injected into and scans the surface of the EUV reticle, and then a corresponding secondary beam, which carries the information of the EUV reticle surface, is emitted and collected by a detector, and finally an image of the EUV reticle surface can be formed by the detector. If defects appear on the image, the defects should be related to the defects of the EUV reticle, so the EUV reticle is inspected to find out the defects of the EUV reticle. According to an aspect of the present invention, the step of conditioning surface charge and the step of inspecting surface are alternatively performed. In one embodiment, a Pre-Conditioning mode is used, and in another embodiment, a Post-Conditioning mode is used. Pre-Conditioning operation means that the step of the conditioning surface charge is performed firstly and the step of inspecting follows. Post-Conditioning operation means that the step of inspecting is performed firstly and the step of conditioning follows. Moreover, the focused primary beam is used to forward scan the EUV reticle surface for inspecting the surface and the primary beam is used to backward scan the surface for conditioning surface charge.

According to an aspect of the present invention, in the scanning step of S10, accumulation of a surface charge of the EUV reticle may be prevented from. In one embodiment, controlling the landing energy is used to avoid the surface charge accumulation. Landing energy is the colliding energy of the focused primary beam on the surface of the EUV reticle. If the landing energy is too small, some electrons of the focused primary beam may be trapped on the surface, or if the landing energy is too large, the electrons of the EUV reticle are excited and emitted out. These conditions cause the accumulation of the surface charge. The accumulation can avoid by controlling the landing energy. In one embodiment, controlling the voltage of the sample stage securing the EUV reticle is used to control the landing energy and make number of the electrons of the focused primary electron beam (primary electrons) equal to the number of the electrons of the secondary beam (secondary electrons). The ratio of secondary electron number to the primary electron number is defined as η (.eta.). Accordingly, in inspecting the surface of the EUV reticle, the electron number of the secondary electron beam can be controlled and make it be equal to the number of the electron number of the focused primary electron beam to prevent the surface of the EUV reticle from charge accumulation.

Figure 2:
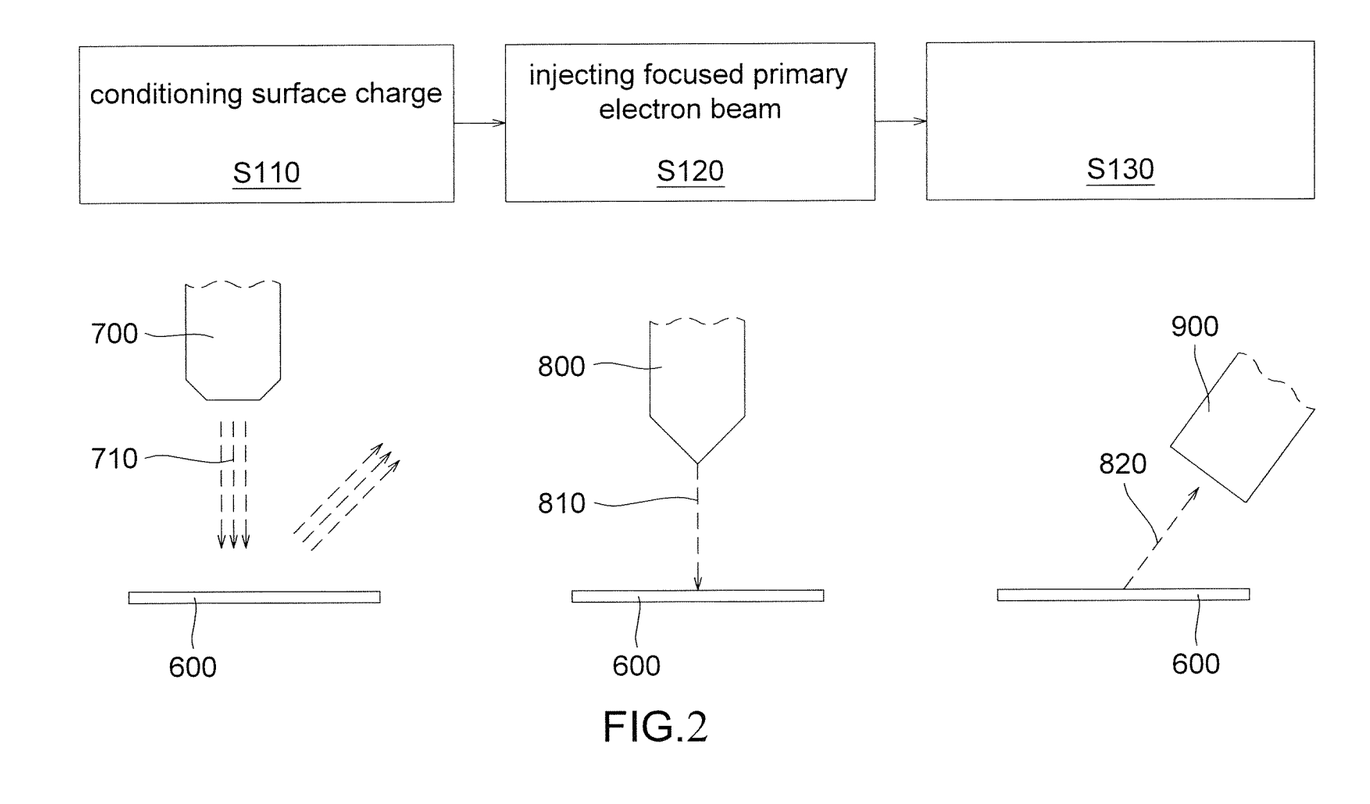
FIG. 2 is a schematic diagram for illustrating the flow chart of scanning an EUV reticle.

FIG. 2 is a schematic diagram for illustrating the flow chart of scanning an EUV reticle. The upper part of the figure shows the flow chart of a scanning process and the lower part of the figure sketches the scenario of the scanning process.

In step of S110, a surface of an EUV reticle is conditioned to neutralize the surface charge. In general, a primary charged particle beam is used.

In step of S120, the surface of the EUV reticle is scanned by a focused primary charged particle beam, such a focused primary electron beam in this embodiment. For enhancing the quality of an image of the inspection, an electron beam is injected into and the electron beam should be focused on the surface of an EUV reticle to get a better accuracy. As shown in figure, a focused electron beam source 800 emits a primary electron beam 810, and then the primary electron beam 810 is injected into and scans the surface of the EUV reticle 600. In one embodiment, an electron beam source emitting an electron beam and a condenser module condensing the electron beam are equipped.

In step of S130, electrons of a secondary electron beam are received to form an image of the surface of the EUV reticle. The surface of the EUV reticle is coated and the coated layer has a specialized pattern. The electrons of the focused primary beam interact with the surface of the EUV reticle. Different location of the surface has different interaction with the injected electrons when the focused primary scans the surface of the EUV reticle. After colliding, the secondary electrons, comprising the back-scattered electrons of the primary focused electron beam or the electrons emitted by the surface of the EUV reticle, carry the information of the surface charge and fly away the surface. The flying electrons form a secondary electron beam and collected by a detector, and then an image can be formed by the secondary electrons.

As shown in the figure, a secondary beam 820 flies away the EUV reticle and enters a detector 900, which provides an image of the surface of the EUV reticle. The electrons of the secondary beam 820 carry the information of the defects of the surface of the EUV reticle 600, and forms the defects of the image provided through the detector 900.

It is emphatically noted that the number of the primary electrons can be controlled by the landing energy and make it be equal to the number of the secondary electrons by controlling the landing energy for avoiding the accumulation of the surface charge.

According to an aspect of the present invention, an apparatus is used to inspect the EUV reticle. The apparatus comprises an electron beam source, a focused electron beam source, deflection module for deflecting the primary electron beam to scan the surface of the EUV reticle, a sample stage for securing the EUV reticle and a detector for collecting the secondary electrons to construct the image of the surface of the EUV reticle.

The apparatus for inspecting the surface of an EUV reticle uses a controllable beam source to provide a low density and high speed electron beam. In general, a heated cathode may emit electrons when heated and the number of the electrons can be controllable by the heating temperature or the current passing the cathode. In the present invention, the temperature or the current passing the cathode is controlled and provides a low density electron gas. A voltage is imposed on the low electron gas to accelerate the electron gas to a direction and pass an aperture to form an electron beam. An electrostatic field and/or a magnetic field are imposed on the electron beam and the electrostatic field and/or a magnetic field can be used to control the focus condition of the electron beam.

An electron beam is used to condition the surface of the EUV reticle by neutralizing the surface charge or regulating the surface to a uniform potential. A focused electron beam is used to inspect the surface of the EUV reticle.

In another embodiment, the primary beam is provided by adjusting position of the sample stage securing the EUV reticle. The focus or the focal point of the focused primary electron beam will move onto or away from the surface of the EUV reticle when adjusting the position of the sample stage.

The invention discloses a method to avoid accumulating surface charge on the surface of an EUV reticle. A landing energy is the energy when a primary electron beam collides the surface of the EUV reticle. Too large or too small landing energy will generate the accumulation of the surface charge. In one embodiment, for controlling the landing energy, a voltage can be imposed on the sample stage, and the imposed voltage of the sample stage can change the potential near the surface of the EUV reticle, which accelerates or decelerates the electrons of the electron beam near the surface, so the landing energy may be controlled by the imposed voltage. Besides, a proper voltage of the sample stage can prevent the EUV reticle from damage caused by over large impact.

A scanning electron microscope (SEM), a swing objective retarding immersion lens (SORIL) SEM or an improved SORIL SEM and so on can be used to implement the apparatus for inspecting the EUV reticle.

A SEM comprises an electron beam source, an aperture module, a condenser lens module, an objective lens module, a deflection module, a sample stage and a detector. The electron beam source generates electron gas and the electrons are accelerated to form an electron gas flow. The electron gas flow passes the aperture to form an electron beam. The electron beam will be condensed by the condenser module and converged into a small section, which is called a primary electron beam (EB). The primary electron beam passes another aperture and is further converged onto the EUV reticle. The deflection module is used to deflect the electron beam and scans the surface of an EUV reticle secured on the sample stage. It is emphatically noted that the focused primary electron beam is modified to have a low beam current density but a high speed (high energy).

It is emphatically noted that a voltage is imposed on the sample stage to change the potential near the surface of the EUV reticle, and the potential will change the landing energy of the primary electron beam. To control the imposed voltage can provide a proper potential and avoid accumulating the charge on the surface of the EUV reticle, that means no charge is accumulated, $\eta$ (.eta.)=1.

When colliding, the electrons of the primary electron beam will interact with the surface of the EUV reticle and condition the surface of the EUV reticle.

After colliding, the electrons fly away the surface with the local information to form a secondary electron beam, and the secondary electron beam enters into the detector. The detector processes the information carried by the secondary electrons to form an image of the EUV surface. If the image has defects, then the defects are related to the defects of the pattern on the surface of the EUV reticle. The accuracy of SEM inspection can reach few nano-meters and satisfy the requirement of nano-level inspection.

The local surface charge will generate a local potential and the local potential will affect electrons of the focused primary electron beam, so the surface charge may reduce the accuracy of an inspection. Therefore, before inspecting the surface of the EUV reticle, a primary electron beam is used to neutralize the surface charges.

Figure 3:
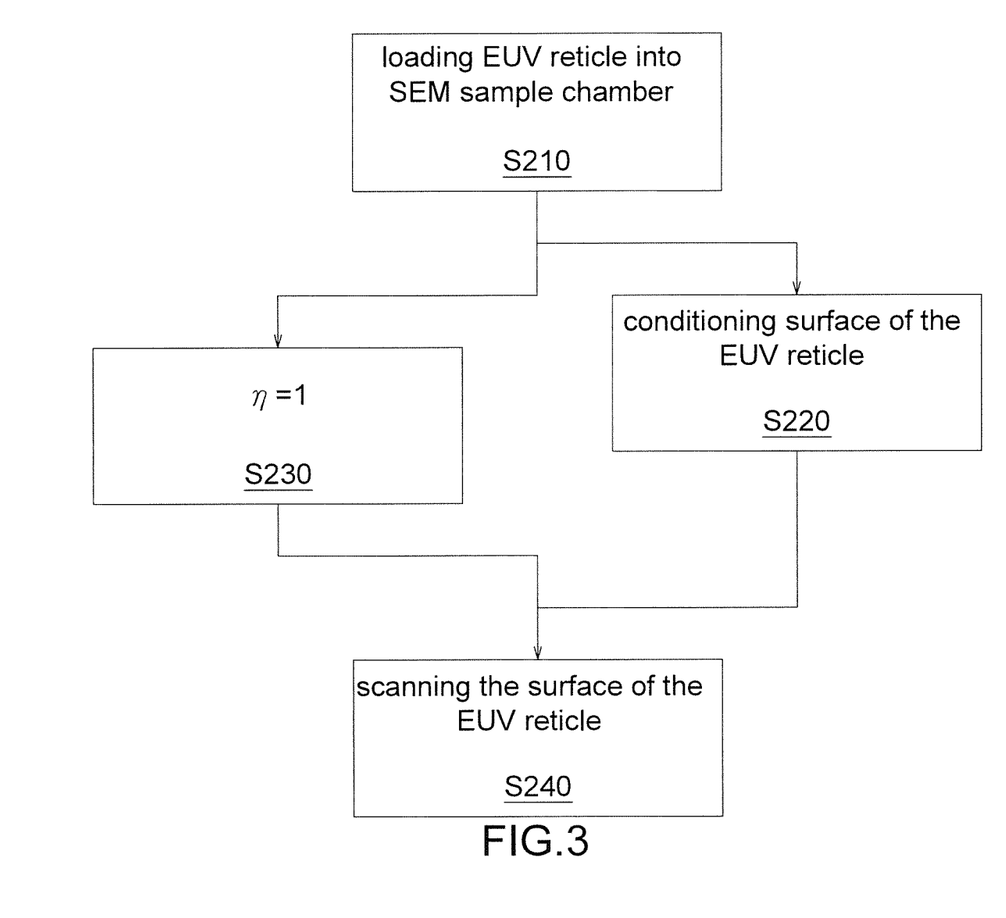
FIG. 3 is a flow chart for illustrating the scanning process according to an embodiment of the present invention.

FIG. 3 is a flow chart for illustrating the scanning process according to an embodiment of the present invention. The embodiment uses an improved SORIL SEM (still called a SEM in this embodiment) as an inspection apparatus, as shown in FIG. 4.

Figure 4:
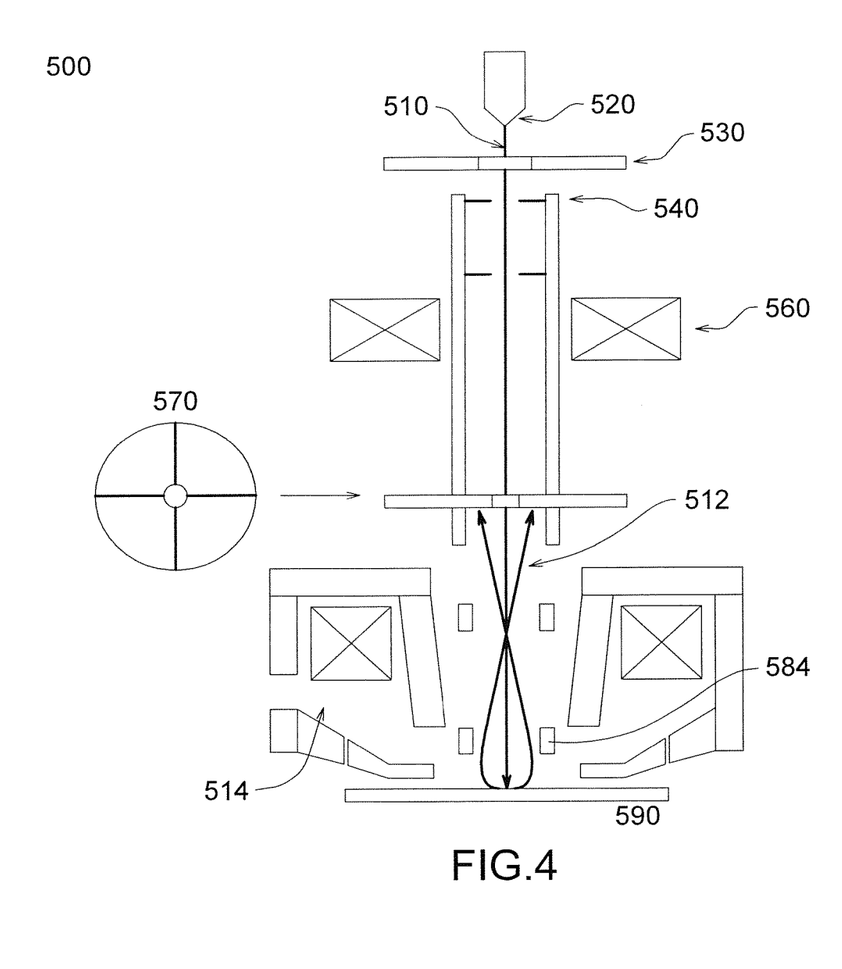
FIG. 4 is a schematic diagram for illustrating the apparatus for inspecting an EUV reticle.

In step of S210, referring FIG. 3 and FIG. 4, an EUV reticle is loaded into the chamber of a SEM 500 and secured on its sample stage 590, hereafter called a sample chamber. The electron beam source 520 emits an electron beam 510, and the current density and the speed of the electrons of the electron beam 510 may be controlled by an electric current and a voltage imposed on the electron beam source 520, called a driving current and a driving voltage. In one embodiment, the driving current only provides a low density beam current and the driving voltage may provide a high speed electron beam 510. The electron beam 510 passes an aperture module 530 and enters an equipotential tube 540, and a condense lens module 560 is equipped with around the equipotential tube 540. Electrons of the electron beam will not be accelerated or decelerated because no voltage is imposed on the electron beam 510. The condense lens module 560 condenses the electrons of the electron beam 510 in a small cross-sectional area to form a collimated and high speed electron beam 510 and then the beam 510 passes the aperture of a detector 570 into the sample chamber. An objective lens module 514 and a deflection module 584 are equipped with around the sample chamber. The objective lens module 514 may focus the electron beam on the surface of the EUV reticle, and the deflection module 584 may deflect the electron beam to scan the EUV reticle secured on the sample stage 590.

For enhancing the accuracy of inspecting the surface of the EUV reticle. Some approaches may avoid accumulation of the surface, two examples, referring to FIG. 3, are illustrated.

In step S220, the surface of the EUV reticle is Pre-Conditioned to neutralize the surface charge of the EUV reticle. The deflection module 584 used to deflect the primary electron beam 510 forward and backward, and the primary electron beam can scan the surface of the EUV reticle. A primary electron beam is used to scan the surface of the EUV reticle to condition the surface charge or to regulate the surface charge to a predetermined condition, such as a predetermined surface potential. Before inspecting, such as Pre-Condition mode, a step of conditioning surface charge is carried out to neutralize the surface charge (to erase the accumulated surface charge) or charge the surface to a predetermined condition. Or, after inspecting, such as Post-Conditioning mode, the step of conditioning surface charge is implemented. Moreover, the focused primary electron beam forward scans the surface of the EUV reticle, and the primary electron beam backward scans the surface charge of the EUV reticle.

Another approach, referring to the step S230 in FIG. 3, is illustrated to avoid surface accumulation. When $\eta$ (.eta.)=1, the number of the focused primary electron beam 510 is equal to the number of the secondary electron beam 512, so no charge is accumulated on the surface. In one embodiment, the sample stage 590 is imposed a voltage to control the landing energy of the focused primary electron beam to make η (.eta.)=1. One of step S220 and step S230 or both can be implemented to enhance the performance of inspection.

After conditioning surface charge, a focused primary electron beam 510 is used to scan the surface of the EUV reticle, referring to step S240 in FIG. 3, and a secondary electron beam 512 caused by the focused primary electron beam 510. The electrons of the secondary electron beam 512 are collected by a detector 570 and generate an image of the surface of the EUV reticle. The pattern of the EUV reticle will create a specific image by using the focused primary electron beam 510 under a specific condition.

In the present invention, the specific image is compared with the original design layout information, such as graphic data system (GDS) or open artwork system interchange standard (OASIS) to align the plurality of patterns on the image and identify the defects on the cap layer or the reflective layer according to the aligned patterns.

Figure 5:
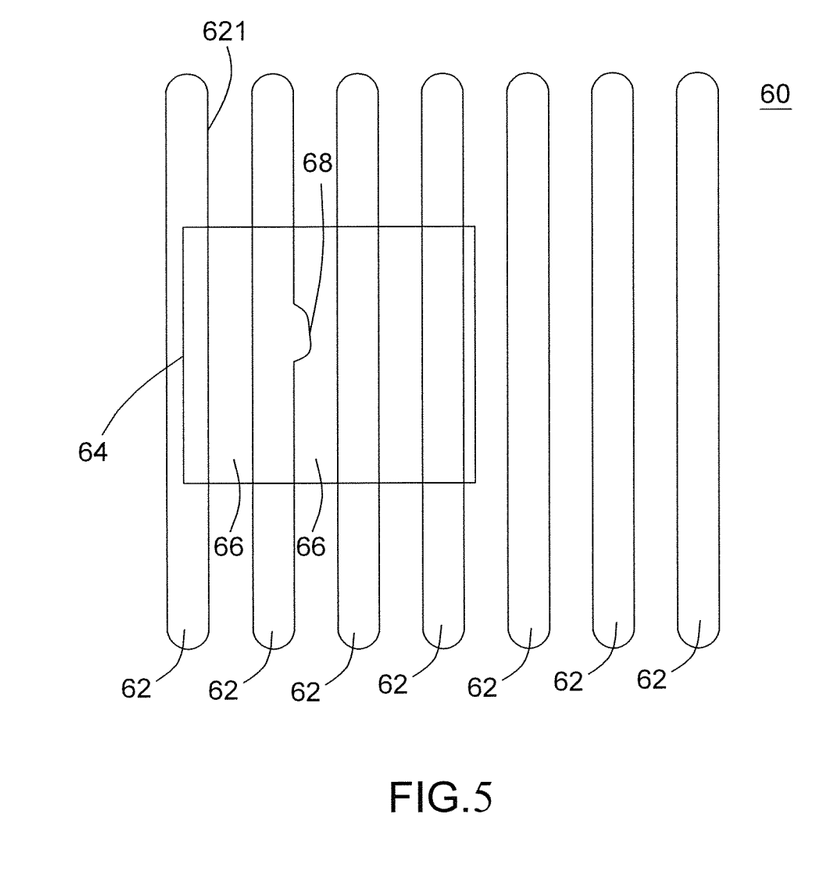
FIG. 5 is a diagram illustrating an image got by scanning the EUV reticle.

FIG. 5 is a diagram illustrating an image got by scanning the EUV reticle, for example. In all of view, the image 60 includes seven circuit pattern 62, but in a square field of view (fov) 64, only the peripheral 621 of a pattern 62 can be show because the greylevel of the circuit pattern 62 and the space 66 between the circuit patterns 62 are the same as η (.eta.)=1. Hence, the defect 68, shown in FIG. 5, can not be identified as concave or convex in this FOV. In the present invention, the GDS information is used to align the patterns 62, so that the circuit pattern 62 may be known and the defects 68 in this embodiment may be identified as a convex with respect to the circuit pattern 62. Furthermore, according to an aspect of the present invention, using GDS information to align patterns, such that the defects may be identified on cap layer of reflective layer of the EUV reticle.

Figure 6:
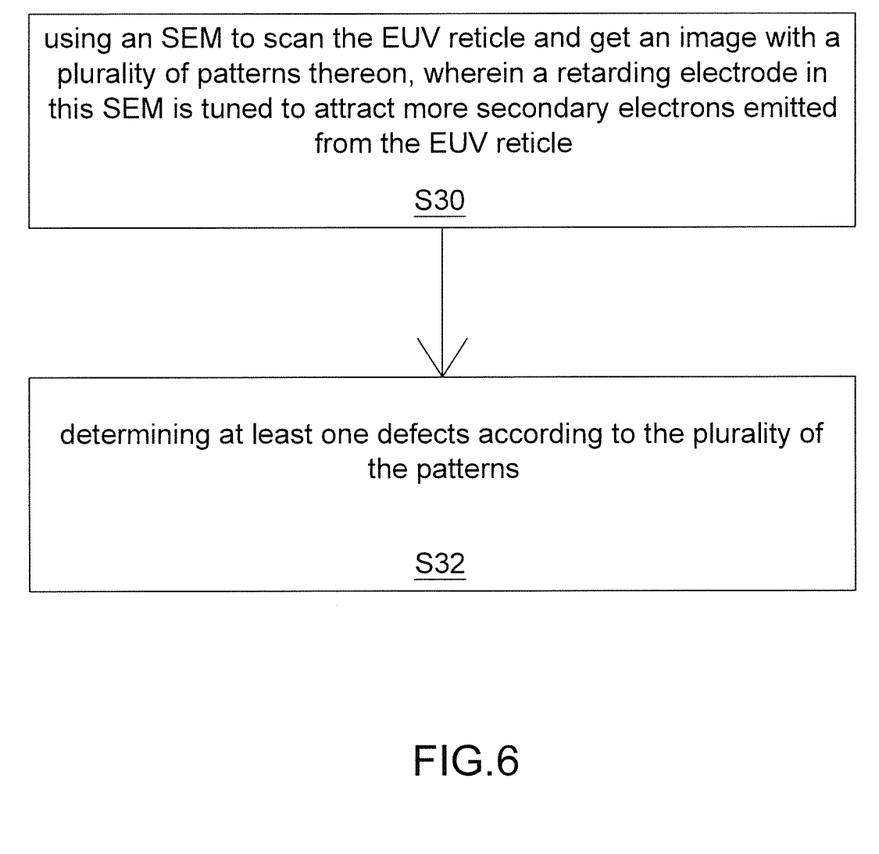
FIG. 6 is a flow chart for illustrating the method for inspecting an EUV reticle according to another embodiment of the present invention.

FIG. 6 is a flow chart for illustrating the method for inspecting an EUV reticle according to another embodiment of the present invention. In this embodiment, in step of S30, using an SEM to scan the EUV reticle and get an image with a plurality of patterns thereon, wherein a retarding electrode in this SEM is tuned to attract more secondary electrons emitted from the EUV reticle, so that the cap layer and the reflective layer, made of different metal, may be shown via different greylevels on the image by tuning the retarding electrode. Hence, in step S32, the defects, which come from the cap layer or the reflective layer may be identified and classified.

Figure 7:
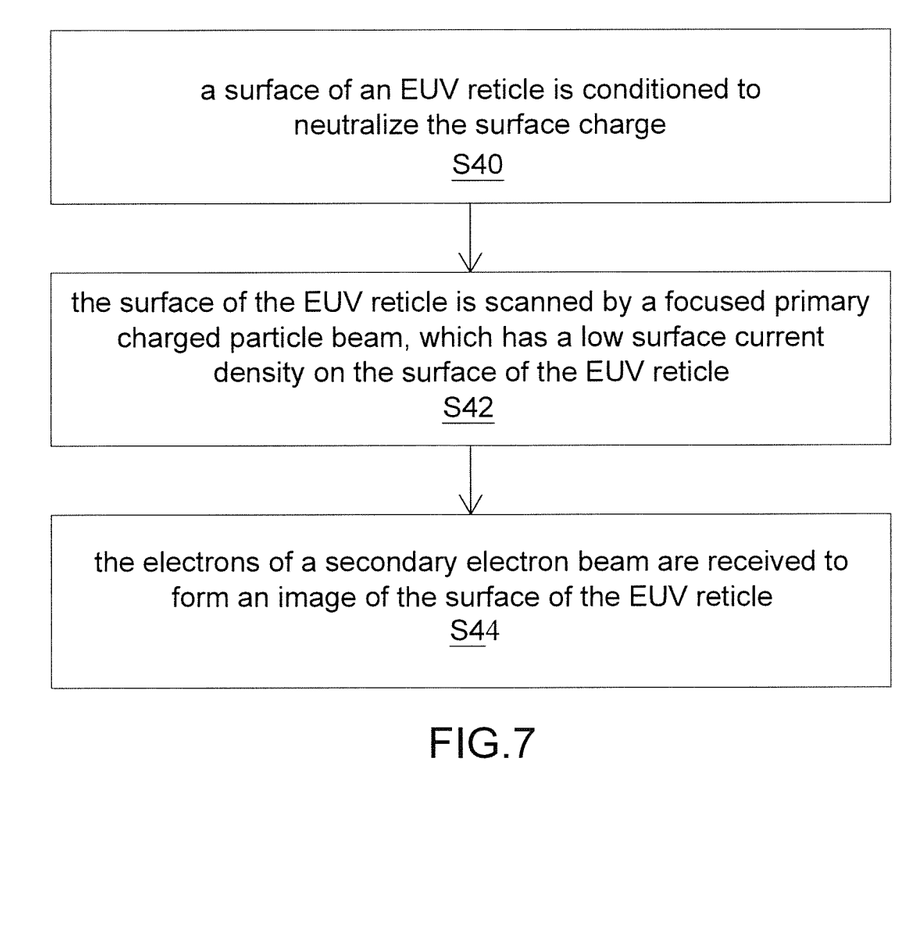
FIG. 7 is a flow chart for illustrating the method for inspecting an EUV reticle according to another embodiment of the present invention.

On the other hand, using high energy electron beam inspection may damage the EUV reticle. In general, the reflectivity loss of the EUV reticle may occur to affect the inspection quality when using high energy electron beam or large current beam density of electron beam. Therefore, an upper limit of surface current density on the surface of the EUV reticle is necessary to avoid the unacceptable reflectivity loss. FIG. 7 is a flow chart for illustrating the method for inspecting an EUV reticle according to another embodiment of the present invention.

In step of S40, a surface of an EUV reticle is conditioned to neutralize the surface charge. In general, a primary charged particle beam is used.

In step of S42, the surface of the EUV reticle is scanned by a focused primary charged particle beam, such a focused primary electron beam in this embodiment. For controlling the reflectivity loss of the EUV reticle, an electron beam is injected into and the electron beam should be focused and have a low surface current density on the surface of the EUV reticle to avoid the reflectivity loss of the EUV reticle. In one embodiment, the low surface current density on the surface of the EUV reticle is less than a value of 2.5325 nA/nm$^2$. For one embodiment, the current value of 1013 nA is the upper limit of the accumulated inspection electron beam current on the same position within an area of 20 nm*20 nm of the EUV reticle.

In step of S44, electrons of a secondary electron beam are received to form an image of the surface of the EUV reticle. The surface of the EUV reticle is coated and the coated layer has a specialized pattern. The electrons of the focused primary beam interact with the surface of the EUV reticle. Different location of the surface has different interaction with the injected electrons when the focused primary scans the surface of the EUV reticle. After colliding, the secondary electrons, comprising the back-scattered electrons of the primary focused electron beam or the electrons emitted by the surface of the EUV reticle, carry the information of the surface charge and fly away the surface. The flying electrons form a secondary electron beam and collected by a detector, and then an image can be formed by the secondary electrons.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for inspecting an extreme ultraviolet (EUV) reticle, comprising:
   scanning an EUV reticle by using a scanning electron microscope (SEM) to get an image with a plurality of patterns thereon;
   receiving an original design layout information to align the plurality of patterns; and
   determining at least one defect directly according to the plurality of aligned patterns.

2. The method according to claim 1, wherein the scanning step comprises:
   conditioning surface charge of a surface of the EUV reticle by using a primary beam;
   injecting a focused primary beam to the surface of the EUV reticle; and
   receiving a secondary electron beam from the surface of the EUV reticle.

3. The method according to claim 2, wherein landing energy of the primary beam, in the step of conditioning surface charge, is adjusted such that number of secondary electron from the secondary electron beam is equal to number of primary electrons from the primary beam.

4. The method according to claim 2, wherein the primary beam, in the step of conditioning surface charge, is provided by a primary beam or a flood gun.

5. The method according to claim 2, wherein the primary beam scans backward in the step of conditioning surface charge, and the focused primary beam scans forward in the step of injecting the focused primary beam.

6. The method according to claim 1, wherein in the scanning step, the SEM uses a primary beam emitting primary electrons to condition surface charge of a surface of the EUV reticle, and uses a focused primary beam to scan the surface of the EUV reticle which emit secondary electrons to inspect the EUV reticle.

7. The method according to claim 6, wherein the number of the primary electrons and the secondary electrons are substantially equal.

8. The method according to claim 6, wherein the SEM is a swing objective retarding immersion lens (SORIL) SEM.

9. The method according to claim 1, wherein the original design layout information comprises graphic data system (GDS) or open artwork system interchange standard (OASIS).

10. The method according to claim 1, wherein the plurality of patterns comprise holes, circuits, devices, or any combination thereof.

11. A method for inspecting an extreme ultraviolet (EUV) reticle, comprising:
using a primary beam emitting primary electrons to condition surface charge of a surface of the EUV reticle;
using a focused primary beam to scan the surface of the EUV reticle which emits secondary electrons;
detecting the secondary electrons from the surface of the EUV reticle to get an image with a plurality of patterns thereon;
receiving an original design layout information to align the plurality of patterns; and
determining at least one defect according to the plurality of aligned patterns.

12. The method according to claim 11, wherein the number of the primary electrons and the secondary electrons are substantially equal.

13. The method according to claim 11, wherein the primary beam, in the step of conditioning surface charge, is provided by a primary beam or a flood gun.

14. The method according to claim 11, wherein the primary beam scans backward in the step of conditioning surface charge, and the focused primary beam scans forward in the step of injecting the focused primary beam.

15. The method according to claim 11, wherein the primary beam and the focused primary beam are provided by an SEM.

16. The method according to claim 15, wherein the SEM is a swing objective retarding immersion lens (SORIL) SEM.

17. The method according to claim 11, wherein the original design layout information comprises graphic data system (GDS) or open artwork system interchange standard (OASIS).

18. The method according to claim 11, wherein the plurality of patterns comprise holes, circuits, devices, or any combination thereof.

19. A method for inspecting an extreme ultraviolet (EUV) reticle, comprising:
scanning an EUV reticle by using a scanning electron microscope (SEM) to get an image with a plurality of patterns thereon, wherein a retarding electrode, between an opening of an objective lens module, in the SEM is tuned to attract more secondary electrons emitted from the EUV reticle; and
determining at least one defect according to the plurality of the patterns.

20. The method according to claim 19, wherein the scanning step comprises:
conditioning surface charge of a surface of the EUV reticle by using a primary beam;
injecting a focused primary beam to the surface of the EUV reticle; and
receiving a secondary electron beam comprising the secondary electrons from the surface of the EUV reticle.

21. The method according to claim 20, wherein the primary beam, in the step of conditioning surface charge, is provided by a primary beam or a flood gun.

22. The method according to claim 20, wherein the primary beam scans backward in the step of conditioning surface charge, and the focused primary beam scans forward in the step of injecting the focused primary beam.

23. The method according to claim 19, wherein the SEM uses a primary beam emitting primary electrons to condition surface charge of a surface of the EUV reticle, and uses a focused primary beam to scan the surface of the EUV reticle which emits the secondary electrons to inspect the EUV reticle.

24. The method according to claim 23, wherein the SEM is a swing objective retarding immersion lens (SORIL) SEM.

25. A method for inspecting an extreme ultraviolet (EUV) reticle, comprising:
conditioning surface charge of a surface of an EUV reticle by using a primary beam;
injecting a focused primary beam to the surface of the EUV reticle, wherein the focused primary beam is adjusted to produce a surface current density on the surface of the EUV reticle so that a reflectivity loss of the EUV reticle is controlled due to the surface current density; and
receiving a secondary electron beam from the surface of the EUV reticle.

26. The method according to claim 25, wherein the primary beam, in the step of conditioning surface charge, is provided by a primary beam or a flood gun.

27. The method according to claim 25, wherein the primary beam scans backward in the step of conditioning surface charge, and the focused primary beam scans forward in the step of injecting the focused primary beam.

28. The method according to claim 25, wherein the primary beam and the focused primary beam are provided by an SEM.

29. A method for inspecting an extreme ultraviolet (EUV) reticle, comprising:
conditioning surface charge of a surface of an EUV reticle by using a primary beam;
injecting a focused primary beam to the surface of the EUV reticle, wherein the focused primary beam is adjusted to produce a surface current density on the surface of the EUV reticle, and the surface current density on the surface of the EUV reticle is less than a value of 2.5325 nA/nm$^2$; and
receiving a secondary electron beam from the surface of the EUV reticle.

30. The method according to claim 29, wherein the primary beam, in the step of conditioning surface charge, is provided by a primary beam or a flood gun.

31. The method according to claim 29, wherein the primary beam scans backward in the step of conditioning surface charge, and the focused primary beam scans forward in the step of injecting the focused primary beam.

32. The method according to claim 29, wherein the primary beam and the focused primary beam are provided by an SEM.

* * * * *